United States Patent
Gulli et al.

[11] Patent Number: 6,158,866
[45] Date of Patent: Dec. 12, 2000

[54] OPTICAL SYSTEM COMBINING IMAGE PRESENTATION AND EYE ANALYSIS

[75] Inventors: Christian Gulli, Castelnau de Medoc; Alain Leger, Merignac; Laurent Bignolles, Bordeaux; Frédéric Lamarque, Paris; Jean-François Le Gargasson, Villiers sur Marne, all of France

[73] Assignee: Thomson -CSF Sextant, Velizy Villacoublay, France

[21] Appl. No.: 09/403,749
[22] PCT Filed: Apr. 28, 1998
[86] PCT No.: PCT/FR98/00851
§ 371 Date: Oct. 29, 1999
§ 102(e) Date: Oct. 29, 1999
[87] PCT Pub. No.: WO98/49592
PCT Pub. Date: Nov. 5, 1998

[30] Foreign Application Priority Data

Apr. 29, 1997 [FR] France ................. 97 05256

[51] Int. Cl.$^7$ ........................................... A61B 3/10
[52] U.S. Cl. .................................................. 351/221
[58] Field of Search ......................... 351/210, 211, 351/214, 213, 215, 216, 221, 205, 206

[56] References Cited

U.S. PATENT DOCUMENTS 4,662,731  5/1987  Yves ..................................... 351/214

*Primary Examiner*—George Manuel
*Attorney, Agent, or Firm*—Oblon, Spivak, McClelland, Maier & Neustadt, P.C.

[57] ABSTRACT

An optical system for presenting an image to a user. The system includes an image source and an optical channel transmitting the image to the user's eye. It also includes an illumination of the ocular fundus and an imaging of the illuminated ocular fundus, both using part of the optical channel. The system enables an analysis of the eye retina observing an image. It also enables depending on the eye position, an adaptation of the visual image presented. If the system is partially mounted in a headset, it enables the presentation of the image to a mobile user.

20 Claims, 2 Drawing Sheets

OPTICAL SYSTEM COMBINING IMAGE PRESENTATION AND EYE ANALYSIS

BACKGROUND OF THE INVENTION

Field of the Invention

The invention relates to systems of presentation of images. The goal of the present invention is notably the improvement of the systems used to present images to a user so that they can be used in a wide range of situations.

SUMMARY OF THE INVENTION

One particular aim of the invention is to exploit image presentation systems in situations where a link must be established between the image presented to the user and parameters related to this user, and notably a link between the image presented and the parameters of the user's eyes. This link can operate in either direction, for example, a modification of the image presented according to the user's viewing direction, or inversely an analysis of the eye during the presentation of an image and according to this image.

More precisely, the invention is an optical system for presenting an image to a user, said system including a source producing image elements to be presented and an optical channel for transmission of these image elements between said source and the eye of the user, characterised in that it also includes a system of illumination of the retina of the eye, and a system of detection of the image on this illuminated retina of the eye, said illumination system and said image detection system using at least part of said optical transmission channel.

The invention can include means of processing the image detected on the illuminated retina of the eye, which notably enables the user's viewing direction to be determined. In this case, according to the invention, said source producing image elements can take account of the viewing direction of the eye. This enables an image better adapted to the situation of observation of the user to be presented.

One example of a source of production of image elements to be presented is a display such as a liquid crystal screen or a cathode ray tube. Another example is a device for direct retinal writing, such as laser beam that scans the retina. These two examples are not limitative.

The part of said optical transmission channel used by the illumination system and the image detection system can be integrated in a head-mounted device. This device is for example a mobile device with a semi-rigid connector, for example a headband/chin-strap, with the eye illuminated or, preferably, a helmet placed on the head of the user; the user of which the image of the retina of the eye is being detected is not then obliged to remain immobile in front of a fixed image display device, his face is simply linked to a head-mounted device in which images are presented. The invention therefore offers the advantage of presenting images to the user while imposing few constrains, for the user retains freedom of head movement. If the system includes a display, this is preferably fitted on the head-mounted device (mobile device or helmet).

The invention also improves the comfort in the use of the image presentation system in a preferred embodiment consisting in moving part of the retinal illumination system and part of the retinal image detection system to some distance from the user's eye, by using an optical transport system including for example a bundle of optical fibers, to enable freedom of movement of the user when observing the image presented, while providing a lightweight head-mounted device.

The invention can be applied to the presentation of the image according to the viewing direction of the observer, notably in a helmet-mounted visual display of an aircraft pilot on which navigation or weapon aiming data are presented.

The invention can also be applied to the analysis of the movement of the eye of a subject reacting to a presentation of images or to the analysis of the retina of the eye of the subject, notably in an ophtalmoscope including a light-weight head-mounted device leaving the subject free to move his head.

The invention is not however limited to the applications mentioned above.

BRIEF DESCRIPTION OF THE DRAWINGS

Other characteristics and advantages of the present invention will appear on reading the description below making reference to the appended drawings which represent a non-limitative, preferred embodiment, in which.

DETAILED DESCRIPTION OF THE PREFERRED EMBODIMENTS

Figure 1:
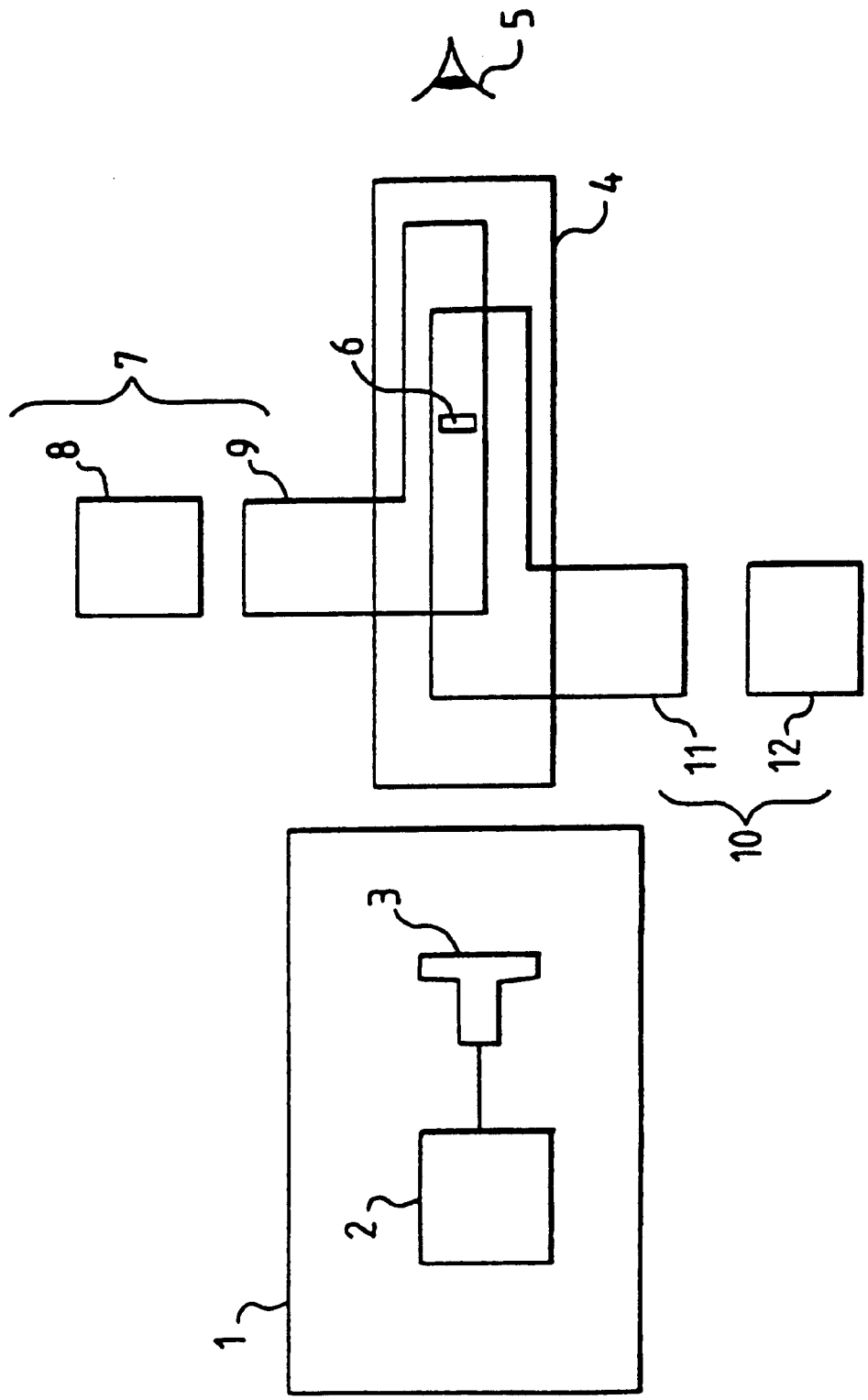
FIG. 1 is a simplified block diagram of an embodiment of the invention.

The simplified drawing in FIG. 1 illustrates a possible embodiment of the optical system according to the invention.

Every image presentation system according to the invention includes a source 1 producing image elements to be presented to the user.

For example, this image source 1 includes an image generator 2 feeding images to a classical display, such as a liquid crystal screen or a cathode ray tube, on the screen 3 of which luminous information is displayed.

The image source 1 according to the invention is obviously not limited to this example.

According to the invention, said luminous information supplied by the image source 1 is transmitted via an optical transmission channel 4 between said image source 1 and the eye 5 of the user. Generally, the optical transmission channel 4 also performs a transformation, such as magnification, collimation or correction of aberrations of said luminous information.

The optical transmission channel 4 enables the eye 5 of the user of the optical system according to the invention to perceive an image.

The optical transmission channel 4 includes an optical device 6 that is, for example, a collimator in the focal plane of which is located the screen 3 of the display, so as to project to infinity the luminous information on the screen 3; the optical channel 4 then enables the eye 5 of the user to perceive information that appears to be located at infinite distance.

The optical transmission channel 4 can also include an optical device 6 that focuses at a finite distance, in which case the user perceives an image that appears to be situated at a finite distance from the eye 5.

The invention also includes an illumination system 7 shown in FIG. 1 that includes a light source 8 and optical transmission system 9 between said light source 8 and the eye 5. The illumination system 7 enables the retina eye 5 of the user to be illuminated.

The illuminated part of the eye is its natural rear inner surface.

Said illumination system 7 preferably operates in the invisible light band, since this has the advantage of not perturbing the user during his observation of the images presented by the image source 1. Said illumination system 7 uses part of the optical transmission channel 4 previously described.

In addition to the illumination of the retina of the eye 5 of the user by the system 7, the invention includes an image detection system 10 that can detect the image on the retina of the eye 5.

In the system 10, an optical unit 11 assures the transmission of at least part of the light wave reflected by the illuminated part of the eye 5, guiding the light from the eye 5 to a device 12 that builds an image of the eye.

Said image detection system 10 uses part of the optical transmission channel 4 previously described.

The invention therefore an image presentation system to be proposed that also provides an image of the retina of the user's eye. The image is preferably that of the natural rear inner surface of the eye.

We shall now describe the invention in a particularly interesting embodiment in which the invention is applied to a visual display device fitted in the helmet of an aircraft pilot.

Generally, a helmet-mounted visual display is a device enabling information to be presented to the person wearing the helmet.

When the wearer is an aircraft pilot, this information is usually superimposed on the background image of the landscape in order to complement or replace the direct view of the landscape through the visor of the helmet, without obliging the pilot to turn his line of sight towards a display in the cockpit. One known embodiment of a helmet-mounted visual display consists in projecting an image on a combiner in front of the pilot's eyes. The combiner function, which can be provided by the visor of the helmet, is a surface that has been treated to make it semi-reflecting such that the projected image is reflected towards the eye of the wearer of the helmet at the same time as the light rays received from the background landscape that are also transmitted by the combiner to the eye of the wearer of the helmet.

The pilot then perceives an image superimposed on the view of the landscape.

The information in this image is for example flight parameters, navigational information, or weapon aiming data.

Certain information are presented in the form of alphanumeric characters, others in the form of symbols.

Information such as the altitude or speed of the aircraft can be presented at a fixed position relative to the face of the wearer of the helmet, whereas other information, such as for example the line of a landing runway, must be consistent with the background landscape observed and the image presented in this case is then different, depending on the direction of observation of the pilot wearing the helmet.

This direction of observation can be estimated by measuring the direction of the aircraft and the relative position of the helmet with respect to this aircraft. Helmets equipped of magnetic position detectors already exist, in which the image presented to the wearer of such a helmet is recalculated taking account of measured positions supplied to the image generator of said helmet.

By measuring the position of the helmet, such known embodiments provide a relatively good estimation of the orientation of the face of the wearer of the helmet; they therefore enable an adaptation of the information presented to the wearer of the helmet whose viewing point is modified only by the displacement of the head, in other words when the orientation of the eyes of the wearer of the helmet is fixed relative to his face.

Such embodiments of the prior art have the disadvantage of ignoring rotational movements of the eye when the pilot changes his point of observation; this is a drawback, since it is a natural tendency to move the eyes before moving the whole head during dynamic observation with the head free.

With such prior art embodiments, the pilot must train himself to move his whole head in order to obtain good coordination of the images. Yet the weight of a helmet is far from negligible, which makes such head movements more tiring and less rapid than eye rotation.

The invention overcomes this disadvantage by taking account of the pilot's viewing direction.

Figure 2:
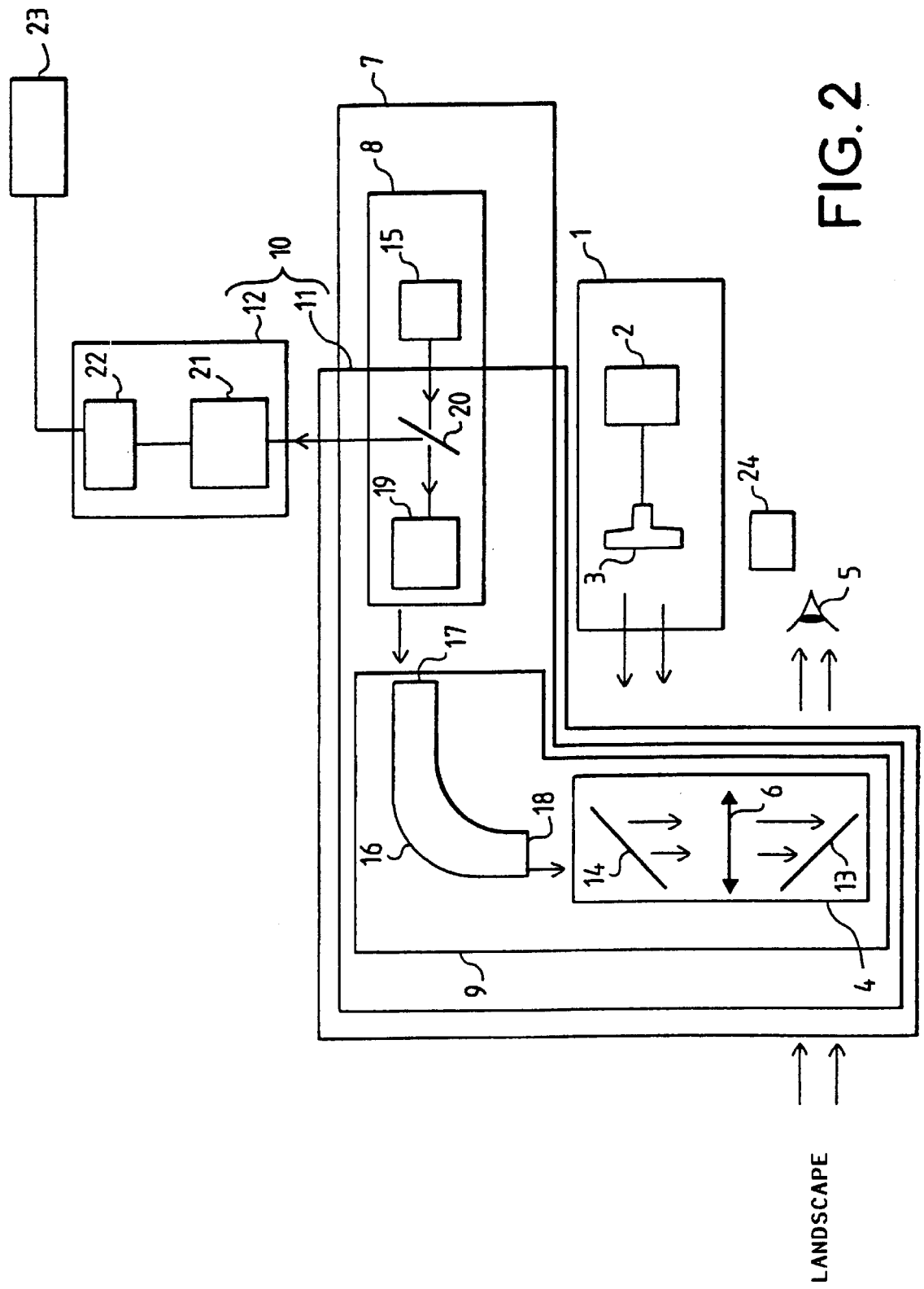
FIG. 2 is a diagram of a helmet-mounted visual display according to the invention including a device for measuring the viewing direction of the user.

A visual display according to the invention, intended for use in the helmet of an aircraft pilot is shown in FIG. 2.

According to the invention, the helmet-mounted visual display includes a source 1 of image elements to be presented.

In the embodiment illustrated in FIG. 2, said source 1 includes, as in the device described with reference to FIG. 1, an image generator 2 feeding images to means of display on the screen 3 on which information is displayed in visible light.

The means of display is for example one of the following non-exhaustive list: a cathode ray tube, a liquid crystal screen (active matrix or not). In this example, we have chosen a cathode ray tube.

The cathode ray tube is here mounted in a helmet, not shown in FIG. 2, worn by the aircraft pilot using the visual display device according to the invention.

The eye 5 of the user of the helmet-mounted visual display is represented in FIG. 2, and it perceives an image from the source 1 via an optical transmission channel 4.

The optical transmission channel 4 includes an optical collimation device 6 whose positioning is such that an image displayed on the screen 3 is projected to infinity.

The optical transmission channel 4 also includes a combiner 13 constituted for example by part of the visor of the helmet.

The eye 5 of the user can therefore observe the landscape directly through the visor and perceive a superimposed image in visible light directed into the eye 5 by the combiner.

Moreover, the instrumental aperture of an optical system is the area in space in which the eye of the user of this optical system must be placed to enable an observation with said system.

As in the use of any optical system, correct perception of the screen 3 by the user of the invention requires the eye 5 to be positioned in the instrumental aperture of the optical transmission channel 4. Here the pupil of the eye 5 lies in the plane of the instrumental aperture of the optical channel 4.

The optical transmission channel 4 is a complex optical system: its weight and dimensions are sufficiently reduced to enable it to be built into the helmet, and it includes lenses for corrections of aberrations and also offers a wide aperture.

The instrumental aperture of the optical channel 4 has for example a diameter two to three times greater than the diameter of the pupil of the eye 5. Typically these diameters are respectively about 15 and 5 millimeters. In the embodiment illustrated in FIG. 2, the optical transmission channel 4 also includes a mirror 14 that reflects the image formed on the screen 3 of the cathode ray tube along the optical axis of the optical collimation device 6.

The optics of the optical channel 4 and the cathode ray tube are placed in the helmet in a manner that provides a weight distribution on the pilot's head that is compatible with the extreme conditions of use of the helmet, such as for example when the pilot ejects from the aircraft.

According to the invention, the helmet-mounted visual display includes an system 7 that illuminates the retina of the eye 5 of the user. The illuminated part is the actual rear inner surface of the eye.

In FIG. 2, the light source 8 of the illumination system 7 illuminates some fibers at a first end 17 of a bundle 16 of optical fibers. The illuminating light wave propagates along these optical fibers to a second end 18 of the bundle 16 of fibers, then propagates, via the optical transmission channel 4 already described and the pupil of the user's eye 5 to reach the retina of the user's eye.

In the illumination system 7 of this particular embodiment of the invention, the transmission optics 9 between said light source 8 and the eye 5 of the user includes the bundle 16 of optical fibers and the optical transmission channel 4.

The second end 18 of the bundle 16 of optical fibers is substantially flat and is situated in the focal plane of the optical collimation device 6 already described.

The illumination of a group A of optical fibers on the first end 17 of the bundle 16 leads to the illumination of a zone B of the retina of the eye 5.

Owing to the collimation, the zone B corresponding to a given group A remains fixed provided the eye 5 makes only translational movements but no rotational movements, while remaining within the instrumental aperture of the optical transmission channel 4.

The light source 8 of the illumination system 7 also includes a scanning system 19 that provides for the successive illumination of different groups A of optical fibers on the first end 17 of the bundle 16 of fibers in order that the illuminated zone B scans the retina. The scanning is preferably of video type.

The scanning system 19 includes for example mechanical scanning by means of a galvanometric mirror.

In the embodiment of the invention illustrated in FIG. 2, the bundle 16 of optical fibers enables the light source 8 to be moved outside the helmet and to some distance from the helmet by means of a detachable connector.

The light source 8 is preferably a source whose wavelengths are limited to the invisible light spectrum in order not to perturb the user.

The light source 8 includes for example an infrared laser diode 15. However the light source 8 is not limited to a coherent light source. In the embodiment described here, the diode laser 15 provides a good level of light energy.

Compared with prior art helmet-mounted visual displays, the system illustrated in FIG. 2 presents the advantage of providing an additional function of illumination of the retina of the eye 5 of the user without significantly increasing the weight.

According to the invention, the system of presentation of an image to the user illustrated in FIG. 2 also includes a system 10 of detection of the image on the illuminated retina of the eye 5. The image is a true image of the actual illuminated retina.

The illuminated zone B of the retina returns a light wave that follows the inverse path of the illuminating wave already described. The wave emitted by the illuminated retina of the eye 5 traverses the optical transmission channel 4, enters the bundle 16 of optical fibers by some fibers of the second end 18 of this bundle 16, and propagates along these fibers to the first end 17 then to the scanning system 19.

In the embodiment described here, the scanning system 19 has not changed its scanning position during the short time required for the light to go back and forth between the scanning system 19 and the retina of the eye 5.

At the output of the scanning system 19, the light reflected by the illuminated zone of the retina of the eye 5 is substantially parallel to the light emitted by the infrared laser diode 15 and it is then reflected by a semi-reflecting mirror 20 in the direction of a device 12 to form an image of the retina of the eye 5. The image is a true image of the actual illuminated retina.

The semi-reflecting mirror 20 reflects much more than it transmits, its characteristic coefficients being for example 0.95/0.05 or even 0.9/0.1, so it favors the light flux returning from the retina of the eye 5, which is substantially less than the flux emitted by the diode laser 15.

In the image detection system 10 according to this particular embodiment of the invention, the optical unit 11, whose definition was given in the description of FIG. 1, includes the optical transmission channel 4, the bundle 16 of optical fibers, the scanning system 19 and the semi-reflecting mirror 20.

Said device 12 includes for example a detector 21 to form an image element and the detector 21 cooperates with a device 22 to build the complete image.

The detector 21 detects the intensity of the light reflected by the illuminated zone B of the retina of the eye 5, for example by means of an avalanche photodiode. The detected intensity depends on the nature of the illuminated cells of the retinal tissue.

The scanning of the retina of the eye 5 by the illuminated zone B enables a video-type image of the whole retinal surface of the eye 5 to be built by successive detection of the emitted light intensity.

The bundle 16 of optical fibers enables the part of the system 10 that builds this retinal image of the eye 5 to be moved some distance away from the helmet.

The retinal image of the eye 5 reveals the vascularity of the retinal tissue with intersecting blood vessels whose topology is specific to each individual and constitutes an optical signature. The blind spot corresponding to the position of the optical nerve can also be located by the imaging device 12.

The helmet-mounted visual display of FIG. 2 therefore offers the advantage of providing a display of the retina of the user's eye which allows for example an analysis of the condition of the retina to identify suitable medical treatments, while leaving free movement to the user whose eye is being examined. Such a user does not have to hold his face fixed in front of a fixed examination apparatus: he can simply wear a helmet incorporating the visual display system previously described that enables an analysis of the eye while allowing head movements.

The image of the retina of the eye 5 supplied by the image detection system has particular characteristics.

First, a translational movement of the eye 5 of the user with respect to the optical transmission channel 4 and therefore relative to the helmet itself does not modify the image of the retina of this eye provided by the device 22.

Secondly, we also note that a rotation of the eye 5 leads to a deformation of the image of the retina of this eye, and that inversely an analysis of this deformation of the image enables an estimation of the rotational displacement of the eye relative to the helmet bearing the visual display system according to the invention.

In FIG. 2, we also note the presence of a device 23 that processes the video image supplied by the device 22.

This image processing by the device 23 consists in analysing a few characteristic points of the retina such as for example the blind spot and about ten intersections of blood vessels. The estimation of the deformation of these characteristic points enables an estimation of the rotation of the eye 5.

The system according to the invention, illustrated by FIG. 2, is used for example to acquire a first image of the retina of the user's eye 5, referred to as the "reference image".

More precisely, this reference image is acquired for example by presenting to the user a particular image with a reticule and asking the user to fix his eyes on the center of this reticule.

Next, the user observes the images presented by the image presentation system of the invention, and the device 23 measures the displacement of a few characteristic points of the retina of the user t estimate the rotation of the eye 5 of the user relative to the reference direction which is that in which the user was looking when the reference image was acquired.

This processing offers the advantage of providing an estimation of any rotation of the eye. This estimation constitutes a measure of rotation of the eye with respect to the helmet in the three directions in space.

The invention therefore enables the construction of a system like the one illustrated in FIG. 2 that assures both a presentation of an image to the user and a measurement of the viewing direction of this user by analysis of the actual retina of the user's eye. It is an oculometer of the retina with a presentation of images using the same optical channel. It has the advantage of being compact.

In an application of a helmet-mounted visual display, the determination of the viewing direction enables control of the source 1 of image elements to be presented so as to modify the image as a function of this direction.

In other applications, the objective may be to analyze the image of the retina of the eye while presenting to the eye an image whose structure or parameters cause the eye to react, for example to change of direction, which are useful for the observation made.

Furthermore, the optical collimation device 6 and the large aperture of the optical transmission channel 4 are such that the measurement of the rotation of the eye relative to the helmet can be made by simply placing on the head the helmet bearing the system according to the invention. In particular, the measurement supplied by the device according to the invention is not sensitive to small lateral displacements, typically of less than ten millimeters, of the helmet relative to the head of the wearer.

The measurement of the viewing direction relative to the helmet of the user, already described, can be in addition to a measurement of the position and orientation of the helmet, for example by means of a magnetic position detection device 24.

For a helmet-mounted visual display of an aircraft pilot, the invention measures the pilot's viewing direction relative to the helmet, the complementary measurement of position and orientation of the helmet being for example made relative to the cockpit by the device 24, and by knowing in addition the orientation of the aircraft the viewing direction relative to the landscape can be computed, which then enables image elements that are consistent with the landscape to be presented to the pilot, by means of the image generator 2.

The complete system illustrated by FIG. 2 presents the advantage of supplying a precise estimation of the viewing direction without imposing stringent constraints on the position of the helmet with respect to the head of the user of the system.

The invention can also be applied for aiming a weapon in the direction indicated by the viewing direction of the pilot.

Using the device 24, the system illustrated in FIG. 2 enables fine analysis of coupled head and eye movements in reaction to a presentation of images, notably when these images are superimposed on a background view of the landscape.

What is claimed is:

1. Optical system for presenting an image to a user, including a source producing image elements to be presented and an optical channel for transmission of these image elements between said source and the eye of the user, characterised in that it also includes a system of illumination of the retina of the eye separate from said source and a system of detection of the image on this illuminated retina of the eye to determine characteristic points of the structure of this retina of the eye, said illumination system and said image detection system using at least part of said optical transmission channel.

2. Optical system according to claim 1, characterized in that said characteristic points are intersections of blood vessels.

3. Optical system according to claim 2, characterized in that one of said characteristic points is the blind spot.

4. Optical system according to claim 2, characterized in that it includes means of processing the retinal image of the eye to determine using this image the viewing direction of the user.

5. Optical system according to claim 1, characterized in that one of said characteristic points is the blind spot.

6. Optical system according to claim 1, characterized in that it includes means of processing the retinal image of the eye to determine using this image the viewing direction of the user.

7. Optical system according to claim 6, characterized in that said part of the optical transmission channel used by said retinal illumination system and said retinal image detection system is mounted in a helmet worn by the user or on some other support whose movements are synchronised with those of the user's head.

8. Optical system according to claim 7, characterized in that said part of the optical transmission channel includes collimation optics enabling an image focused at infinity to be presented to the eye of the user.

9. Optical system according to claim 8, characterized in that said source producing image elements includes a display placed in the focal plane of said optics.

10. Optical system according to claim 9, characterized in that said display is fitted to said helmet worn on the head of the user.

11. Optical system according to claim 7, characterized in that said part of the optical transmission channel includes focusing optics that focus at a finite distance enabling an image appearing to be located at a finite distance to be presented to the eye of the user.

12. Optical system according to claims 11, characterized in that said source producing image elements is a light bundle, operating in the visible light band, associated with means of scanning that enables an image to be directly written on the retina of the eye of the user.

13. Optical system according to claim 7, characterized in that said retinal illumination system and said retinal image detection system are in part installed outside said helmet thanks to the use of transport optics.

14. Optical system according to claim 13, characterized in that said transport optics include a bundle of optical fibres.

15. Optical system according to claim 6, characterized in that said source producing image elements to be presented takes account of the viewing direction of the user.

16. Optical system according to claim 1, characterized in that said system illuminating the retina of the eye includes a light source associated with means of scanning.

17. Optical system according to claim 16, characterized in that said light source is an infrared source.

18. Optical system according to claim 16 or 17, characterized in that said retinal image detection system includes means of detection of the intensity of the light emitted by the retina of the eye illuminated by said light source.

19. Optical system according to claim 18, characterized in that said retinal image detection system also includes means of scanning to build said retinal image.

20. Optical system according to claim 19, characterized in that said means of scanning used in said retinal illumination system and said means of scanning used in said retinal image detection system are the same.

* * * * *